United States Patent [19]
Kern

[11] Patent Number: 6,116,737
[45] Date of Patent: Sep. 12, 2000

[54] ABLATION PROFILE CALIBRATION PLATE

[75] Inventor: William I. Kern, Longwood, Fla.

[73] Assignee: LaserSight Technologies, Inc., Winter Park, Fla.

[21] Appl. No.: 09/482,555

[22] Filed: Jan. 13, 2000

Related U.S. Application Data

[60] Provisional application No. 60/115,848, Jan. 13, 1999.

[51] Int. Cl.[7] .................................................. A61B 3/10
[52] U.S. Cl. ................................................. 351/212; 606/5
[58] Field of Search ................................. 351/212; 606/4, 606/5; 530/356; 128/898

[56] References Cited

U.S. PATENT DOCUMENTS

| | | |
|---|---|---|
| 2,972,278 | 2/1961 | Bingley . |
| 4,200,395 | 4/1980 | Smith et al. . |
| 5,095,384 | 3/1992 | DeNatale . |
| 5,277,911 | 1/1994 | Viegas et al. . |
| 5,324,281 | 6/1994 | Muller . |
| 5,464,960 | 11/1995 | Hall et al. . |
| 5,480,396 | 1/1996 | Simon et al. . |
| 5,571,107 | 11/1996 | Shaibani et al. . |
| 5,582,752 | 12/1996 | Zair . |
| 5,713,893 | 2/1998 | O'Donnell, Jr. . |
| 5,723,142 | 3/1998 | Bowyer . |
| 5,735,843 | 4/1998 | Trokel . |
| 5,772,656 | 6/1998 | Klopotek . |
| 5,776,359 | 7/1998 | Schultz et al. . |
| 5,779,696 | 7/1998 | Berry et al. . |
| 5,833,701 | 11/1998 | Gordon . |
| 5,861,486 | 1/1999 | Devore ................................. 530/356 |

*Primary Examiner*—George Manuel
*Attorney, Agent, or Firm*—William H. Bollman

[57] ABSTRACT

A profiling and/or calibration sample plate allowing approximately full scale calibration monitoring of an ablation achieved in corneal tissue. The profiling/calibration sample plate also allows for a permanent record of an achieved corneal ablation to be made immediately before (and/or during) the actual cornea to be ablated is ablated. The present invention allows "in vitro" full scale determination of the ablation profile resulting from a given set of refractive laser parameters. One exemplary profiling/calibration sample plate includes a plate (or other shape) having a recess adapted to contain a cross-linked collagen material. The collagen material serves as an approximation of corneal tissue having a similar ablation rate to allow for a "full scale" calibration and/or measurement of an ablation procedure as it will actually occur in a cornea. The profiling/calibration sample plate may include alignment registration elements to allow precise positioning of the calibration plate with respect to an astigmatism or other directional optical component if included in the ablation profile. A non-contact interferometer may be used to measure the resultant or achieved ablation profile on the surface of the cross-linked collagen material contained in the profiling/calibration sample plate. The measured surface features in the collagen material and/or a preserved original or copy of the cross-linked collagen material may be maintained as a permanent record of the actual ablation performed on a particular patient.

24 Claims, 3 Drawing Sheets

CALIBRATING PLATE

ABLATION PROFILE CALIBRATION PLATE

The present application claims priority from U.S. Provisional Application Ser. No. 60/115,848, entitled "Profiling Calibration Plate", filed on Jan. 13, 1999, the complete specification and drawings of which are expressly incorporated herein by reference.

BACKGROUND OF THE INVENTION

1. Field of the Invention

This invention relates generally to "in vitro" analysis to accurately measure the resultant ablative profile of corneal tissue to be reshaped by ablation, allowing the capability to compare a measured (i.e., achieved) ablation profile against the intended profile. The present invention further relates to the ability to determine any differences between the achieved ablation profile and the intended ablation profile to provide information allowing adjustment to an ablation laser's operating parameters to correct for any differences. The present invention additionally relates to the creation of a permanent record of an achieved ablation profile.

2. Background of Related Art

Currently refractive laser systems used to ablate human corneal tissue are calibrated utilizing a flat sheet of polymethyl-methacrylate (PMMA) material. In such a system, a refractive correction is ablated onto the surface of the PMMA plate using an ultraviolet (UV) laser beam source, and the achieved refractive power of the ablated area is measured with a lensometer. Ablation profiles achieved in PMMA material have generally been measured utilizing either a lensometer or a surface profiling system, e.g., a surface scanning instrument manufactured by Tencor Instruments, and extrapolated to predict the refractive power that would be achieved from the reshaped corneal surface. The PMMA correction achieved (typically expressed in diopters) is compared to the desired, or target, corneal correction.

Unfortunately, one problem with utilizing PMMA for this type of calibration is the fact that PMMA material when exposed to UV laser radiation has an ablation rate that is approximately 25% of the ablation rate of human corneal tissue. For example, a target ablation of 10 diopters on human corneal tissue results in an actual achieved test ablation of only about 2.5 diopters when performed on the conventional PMMA calibration material.

For this reason, UV ablation of PMMA material can be effectively utilized only for calibration of a refractive laser system: not to measure an actual ablation profile intended for human corneal tissue. For instance, test ablations are performed using a conventional PMMA material to verify standardized laser system performance on a day to day basis or between cases. As an example, a series of test ablations performed in PMMA material utilizing the same system parameters can be a reasonable verification of day to day equivalent system performance when the ablating laser is operated at those exact test parameters.

Unfortunately, since PMMA ablates at a rate equivalent to approximately 25% of the rate on human corneal tissue, this calibration technique is insensitive to slight changes in system parameters, including those which may affect the performance in corneal tissue but which may not be evident in the ablation of a calibration material at a fraction of the ablation rate.

U.S. Pat. No. 5,464,960 to Hall et al., is an example of a laser calibration device which uses PMMA material. According to Hall et al., a laser is aimed at a monolayer thin film of PMMA material spin coated over a crown glass slide. The number of laser pulses needed to remove the coating over an area of the film, signaled by a sudden fluorescence as the laser reaches the underlying glass, is used as a calibration factor. This calibration factor is obtained by dividing the thickness of the monolayer film by the number of ablation laser pulses used to reach the sudden fluorescence. Other calibration factors are obtained for the various areas of the targeted surface until the entire area reaches fluorescence. Any spread between these various calibration factors provide a map of the ablative characteristics of the laser beam across its entire width based on an achieved profile in the PMMA material. However, the ablative characteristics might be significantly different if determined based on an ablation of corneal tissue, which has an ablation rate about four (4) times that of the PMMA calibration material.

There is a need for an improved capability for predicting, measuring and recording an ablation profile achieved in corneal tissue.

SUMMARY OF THE INVENTION

In accordance with the principles of the present invention, a permanent ablation profile recordation system comprises a collagen material adapted for ablation with an ablating laser beam in accordance with an ablation profile determined for application to corneal tissue. The collagen material has an ablation rate approximately equal to that of the corneal tissue.

A method of profiling a laser ablation of corneal tissue in accordance with another aspect of the present invention comprises ablating a collagen material with an ablating laser beam in accordance with an ablation profile determined for application to corneal tissue. The collagen material has an ablation rate approximately equal to that of the corneal tissue. An actual ablation profile achieved in the collagen material is measured.

A method of optimizing a laser ablation of corneal tissue in accordance with another aspect of the present invention comprises ablating a collagen material with an ablating laser beam in accordance with an ablation profile determined for application to corneal tissue. The collagen material has an ablation rate approximately equal to that of the corneal tissue. An actual ablation profile achieved in the collagen material is measured and the measured profile utilized to determine if more or less treatment is required to achieve the desired ablation profile in corneal tissue.

BRIEF DESCRIPTION OF THE DRAWINGS

Features and advantages of the present invention will become apparent to those skilled in the art from the following description with reference to the drawings, in which.

DETAILED DESCRIPTION OF ILLUSTRATIVE EMBODIMENTS

Figure 1:
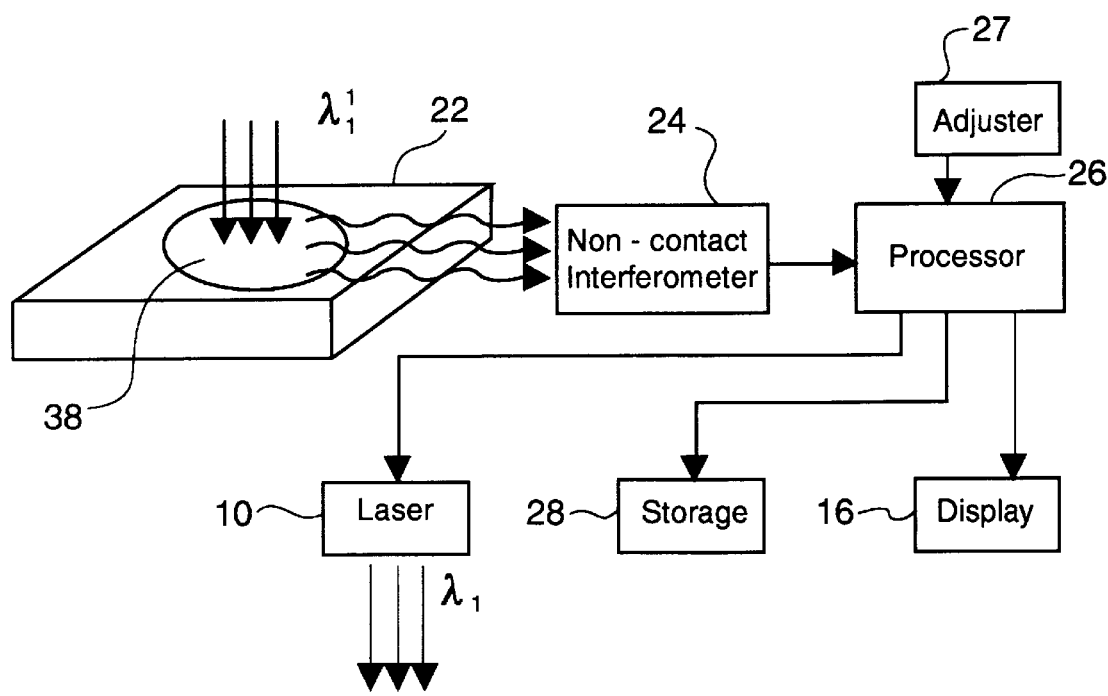
FIG. 1 illustrates the calibration system for the profiling calibration system.

The present invention results from a recognition that abaltions performed utilizing specifically formulated collagen material together with an accurate measurement of the resultant ablative profile would provide an effective confirmation that a particular refractive laser system about to perform an actual ablation procedure on corneal tissue, will perform according to specification and achieve the intended results. Moreover, comparison of the measured (achieved) ablation profile as would actually be achieved in corneal tissue against the intended profile would offer an additional advantage over systems which are tested using a material having an ablation rate significantly different from that of a corneal surface. Determining any differences between the achieved and intended ablation profile would provide important information allowing adjustment of the refractive laser's operating parameters to correct for the differences. Moreover, a permanent record of the actual ablation profile as was performed in corneal tissue can be permanently recorded for subsequent evaluation and can become part of the patient's medical records.

The present invention provides a method and apparatus for accurate "in vitro" determination of an actual ablation profile as performed in corneal tissue resulting from a given set of refractive laser system parameters. The invention provides a method and apparatus to confirm the performance of the laser system as it will perform in corneal tissue immediately prior to its use for human corneal ablation. Use of the method and apparatus will enable a physician to determine whether the profile of the achieved test ablation corresponds as desired to the intended ablation profile. The invention also allows for a permanent record of an actual corneal ablation, not merely a 25% calibration estimate as in the prior art. The permanent record can document the performance of the ablating laser system immediately prior to each human corneal ablation.

A more accurate ablation result can be achieved on human corneas utilizing this method and apparatus by measuring the results of the achieved ablation profile, and by calibrating the relevant refractive laser system based on "full scale" results, not on results used for calibration purposes as in the prior art. Measurement of the "full scale" test ablation profile can confirm that the achieved profile corresponds to the intended profile, before the human cornea is treated with the same system pameters.

In accordance with the principle of the present invention, the intended profile is ablated onto a profiling/calibration plate containing a specimen of cross-linked collagen material. Then, the resulting ablation profile is measured, utilizing one of several available types of surface profiling instruments, preferably a non-contact interferometer such as the PD-1000 available from Precision-Dynamics, Inc., Burlington, Ontario, Canada. Using the achieved ablation profile, the laser system operating parameters can be confirmed or adjusted based on the full scale measurements. Moreover, a display may be used to display, and store, the achieved ablation profile.

The present invention incorporates a cross-linked collagen material for use as an in-vitro ablation test pad simulating an actual cornea with a similar ablation rate. Certain formulations of cross-linked collagen material have been found to exhibit rates of ablation similar to human corneal tissue when exposed to UV wavelengths. For instance, U.S. Pat. No. 5,723,142, explicitly incorporated herein by reference, discloses a cross-linked collagen material exhibiting ablation properties similar to those of a human cornea.

The collagen material utilized in the disclosed embodiment of the present invention is preferably a special formulation of such cross-linked collagen material (e.g., as disclosed in U.S. Pat. No. 5,723,142 ("the '142 patent") that has been stabilized to remain solid through a specified temperature range. Moreover, it is desired that the collagen material be modified to remain free of biological growth and/or contamination throughout its shelf life.

A first element of the method and apparatus is to form a profiling/calibration sample plate. An exemplary profiling/calibration plate can be produced from, e.g., molded plastic containing a recess. In the disclosed example, the recess is approximately 10 mm in diameter by approximately 0.3 mm deep. Collagen material is placed in the recess.

In one embodiment, the surface of the cross-linked collagen material is flat and approximately aligned to an upper surface of the profiling/calibration sample plate. Moreover, the cross-linked collagen material may be sealed and protected by a pull-off tab or other easy removal means which may be applied to seal the surface of the profiling/calibration plate.

The disclosed profiling/calibration sample plate is embossed with alignment marks and polar coordinates that can be utilized to determine, or align, the axis of astigmatism should the desired refractive correction obtained by the ablation profile contain an astigmatic, or cylindrical, component.

Each profiling/calibration plate may be individually packaged and sealed in a light and moisture resistant package, for example, in a foil packaging material. The packaging material also preferably carries the appropriate labeling.

A second element of the present invention is a means for measuring the actual, achieved profile ablated on a profile/calibration sample plate which closely resembles the ablation characteristics of corneal tissue. For instance, an interferometer-based instrument may be used. An interferometer is a non-contact instrument capable of measuring the profile of an ablated surface with sub-micron accuracy. Preferably, the interferometer will include a specimen stage with movement in the X, Y and θ axes. The instrument may be used to measure the actual ablation profile from the profiling/calibration sample plate as a "full scale" approximation of the ablation which will actually be achieved in corneal tissue.

After the achieved ablation has been measured, the achieved ablation profile can be displayed, printed, or otherwise recorded as a permanent full scale record of the achieved ablation. Moreover, the profiling/calibration sample plate may be appropriately sealed, preserved and stored to serve as a model of the actual ablation performed on a patient's cornea.

Preferably, a comparison of the intended versus the achieved ablation profile can be displayed to show any differences to allow for subsequent correction before any procedure is performed on an actual cornea.

FIG. 1 shows an exemplary embodiment of a corneal ablation profiling/calibration sample plate in accordance with the principles of the present invention.

In particular, a profiling/calibration plate 22 contains cross-linked collagen material 38 as disclosed in the '142 patent. The cross-linked collagen material 38 is subjected to an ablation procedure. Afterwards, a non-contact interferometer 24 and/or other surface measuring tool is used to measure the resultant ablation achieved in the cross-linked collagen material 38, e.g., by measuring the spectral structure of the remaining upper surface of the cross-linked collagen material 38.

In accordance with the principles of the present invention, it is also possible to adjust an ablation procedure in real time based on measurements of a cross-linked collagen material 38 ablated in parallel with the cornea. For instance, a processor 26 can receive an appropriate measurement signal from the non-contact interferometer 24, which it can use to control suitable aspects of the ablating laser 10 via an ablation adjustment module 27. The processor 26 may also supply a suitable measurement signal from the non-contact interferometer 24 to a storage device 28 and/or to a display 16. Physical storage of the measurement signal (e.g., in the form of a printout) could become part of a patient's permanent medical record.

Figure 2A:
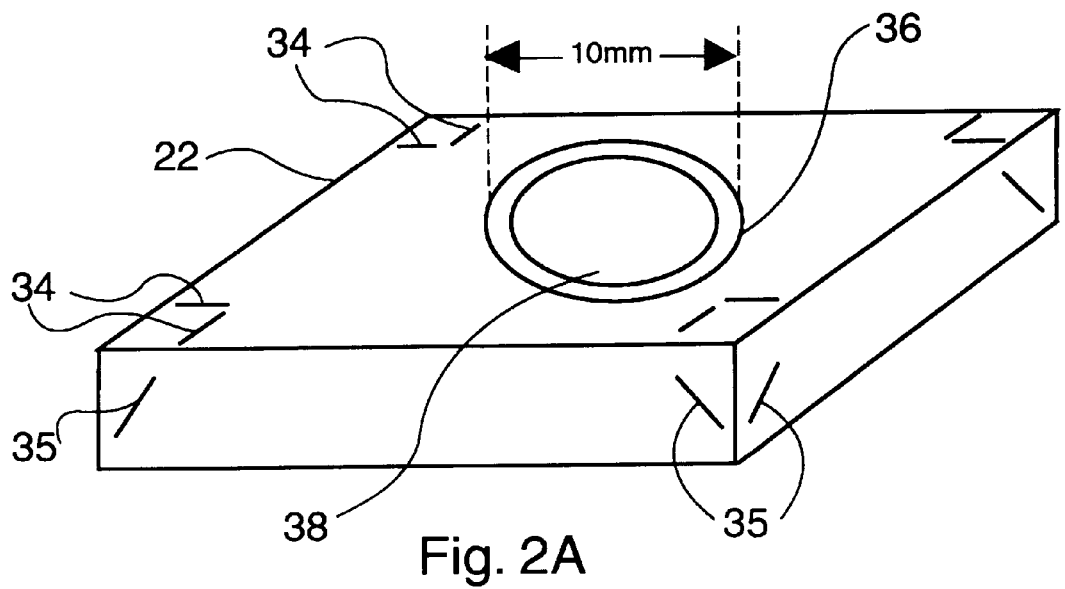
FIGS. 2A to 2C show a calibration plate used in conjunction with the present invention.
Figure 2B:
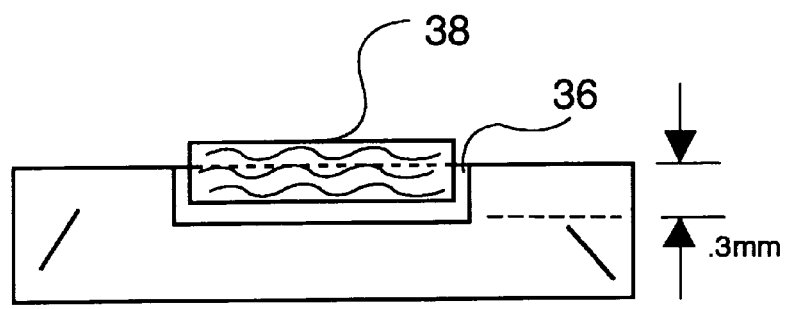
Figure 2C:
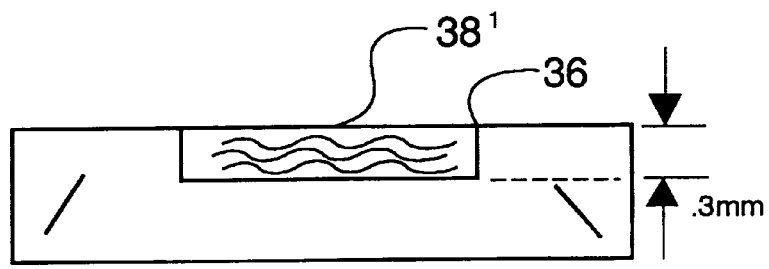

FIGS. 2A to 2C show an exemplary calibration/profiling sample plate 22.

In particular, as shown in FIG. 2A, the calibration plate 22 may be a flat plate produced from molded plastic, or the like. A deep recess 36 is formed in the profiling/calibration sample plate 22 and preferably sized to contain a sufficient amount of cross-linked collagen material 38.

In FIG. 2B, the collagen material 38 is shown as being slightly thicker than the depth of the recess 36.

In FIG. 2C, the surface of the collagen material 38' is substantially flat and aligned to the upper surface of the plate.

The profiling/calibration sample plate 22 is preferably embossed or otherwise marked with alignment marks 34 and/or polar coordinates 35 that can be utilized to determine, or align, an axis of astigmatism according to a desired refractive correction.

Figure 3:
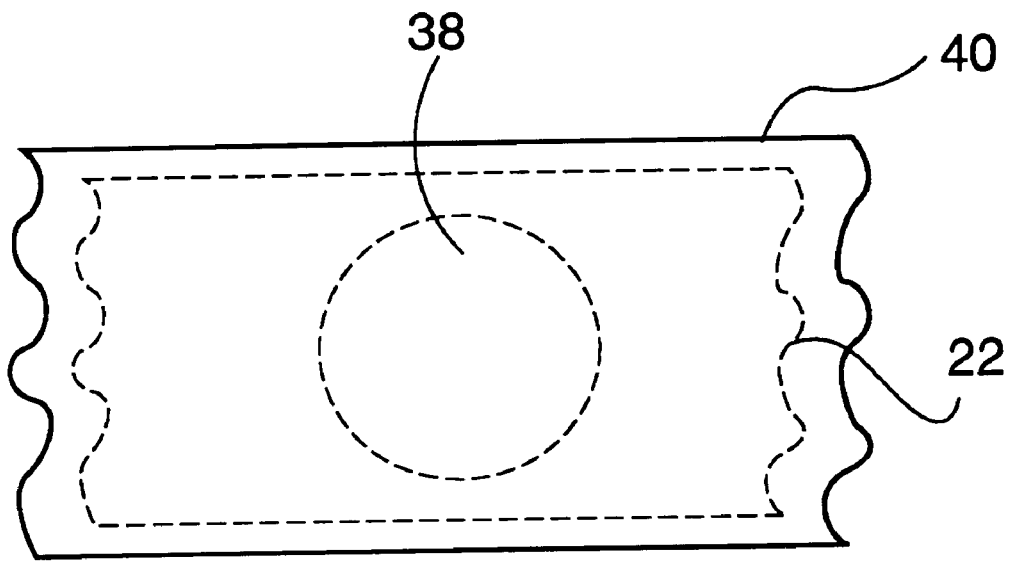
FIG. 3 shows the packaging which contains the calibration plate used in conjunction with the present invention.
Figure 4:
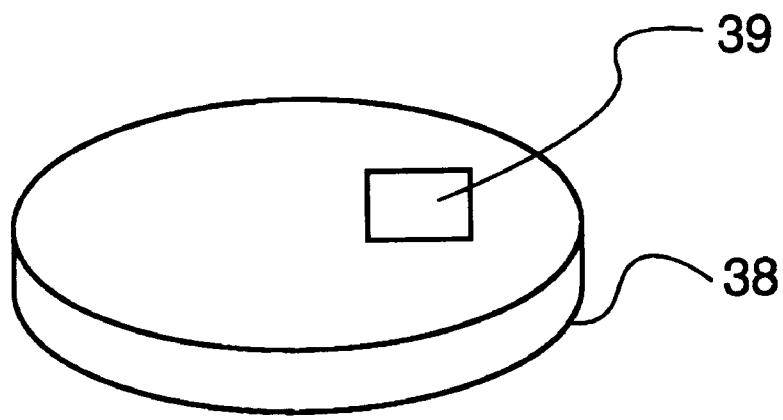
FIG. 4 shows a single use collagen material having a pull tab cover.

FIG. 3 shows that each profiling/calibration sample plate 22 may preferably be individually packaged and sealed in a light and moisture resistant package 40. The packaging itself may be of the foil type or other type of flexible and/or opaque packaging material. The packaging material can also carry the appropriate labeling as required or desired by local and/or national standards.

The cross-linked collagen material (38, 38') contained in the package 40 is preferably protected by a cover including, e.g., a pull-off tab 39 or other easy removal means applied to the packaging of the profiling/calibration sample plate 22.

Another application for the collagen profile/calibration plate is for measurement and/or calibration of the energy, or fluence, of a laser system. By modifying the above-described plate to contain a known thickness of collagen material, a laser system's fluence can be determined by counting the number of laser pulses, delivered consecutively to the same area, that are required to ablate the collagen material to that know depth. The resultant calculation can be utilized to determine fluence or sent through a fed back loop to the laser system to be used for calibration.

It is to be understood that the provided illustrative examples are by no means exhaustive of the many possible uses for my invention. Thus, while the invention has been described with reference to the exemplary embodiments thereof, those skilled in the art will be able to make various modifications to the described embodiments of the invention without departing from the true spirit and scope of the invention.

What is claimed is:

1. A permanent ablation profile recordation system, comprising:

a collagen material adapted for ablation with an ablating laser beam in accordance with an ablation profile determined for application to corneal tissue, said collagen material having an ablation rate approximately equal to that of said corneal tissue.

2. The ablation profiling system according to claim 1, further comprising:

an interferometer adapted to measure and store refractive information regarding an actual ablation profile achieved in said collagen material.

3. The ablation profiling system according to claim 2, further comprising:

a printer adapted to print said refractive information to provide a permanent record of said actual ablation profile.

4. The ablation profiling system according to claim 1, further comprising:

a profiling/calibration plate including a recess adapted to contain said collagen material.

5. The ablation profiling system according to claim 4, wherein said profiling plate further includes:

an alignment registration element adapted to allow precise positioning of said profiling plate.

6. The ablation profiling system according to claim 1, wherein:

said collagen material is a cross-linked collagen material.

7. The ablation profiling system according to claim 1, wherein:

said collagen material remains solid through a predetermined temperature range.

8. A method of profiling a laser ablation of corneal tissue, comprising:

ablating a collagen material with an ablating laser beam in accordance with an ablation profile determined for application to corneal tissue, said collagen material having an ablation rate approximately equal to that of said corneal tissue; and measuring an actual ablation profile achieved in said collagen material.

9. The method of profiling a laser ablation of corneal tissue according to claim 8, wherein:

said collagen material is a cross-linked collagen material.

10. The method of profiling a laser ablation of corneal tissue according to claim 8, further comprising:

preserving said collagen material after ablation as a long-lasting record of said actual ablation profile achieved.

11. The method of profiling a laser ablation of corneal tissue according to claim 8, further comprising:

comparing an intended refractive correction to said actual ablation profile achieved in said collagen material before a refractive correction ablation profile is performed in said corneal tissue.

12. The method of profiling a laser ablation of corneal tissue according to claim 8, further comprising:

placing said collagen material in a recess of a profiling plate before said ablation with said laser beam.

13. The method of profiling a laser ablation of corneal tissue according to claim 8, further comprising:

splitting said ablating laser beam to provide a first split beam adapted to ablate said collagen material and a second split beam adapted to ablate said corneal tissue; wherein said collagen material and said corneal tissue are substantially simultaneously ablated.

14. The method of profiling a laser ablation of corneal tissue according to claim 13, wherein:

said collagen material is a cross-linked collagen material.

15. The method of profiling a laser ablation of corneal tissue according to claim 8, further comprising:

printing a representation of said measured actual ablation profile achieved in said collagen material.

16. Apparatus for profiling a laser ablation of corneal tissue, comprising:

means for ablating a collagen material with an ablating laser beam in accordance with an ablation profile determined for application to corneal tissue, said collagen material having an ablation rate approximately equal to that of said corneal tissue; and means for measuring an actual ablation profile achieved in said collagen material.

17. The apparatus for profiling a laser ablation of corneal tissue according to claim 16, wherein:

said collagen material is a cross-linked collagen material.

18. The apparatus for profiling a laser ablation of corneal tissue according to claim 16, further comprising:

means for preserving said collagen material after ablation as a long-lasting record of said actual ablation profile achieved.

19. The apparatus for profiling a laser ablation of corneal tissue according to claim 16, further comprising:

means for comparing an intended refractive correction to said actual ablation profile achieved in said collagen material before a refractive correction ablation profile is performed in said corneal tissue.

20. The apparatus for profiling a laser ablation of corneal tissue according to claim 16, further comprising:

means for placing said collagen material in a recess of a profiling plate before said ablation with said laser beam.

21. The apparatus for profiling a laser ablation of corneal tissue according to claim 20, further comprising:

means for registering said profiling plate with respect to said laser beam.

22. The apparatus for profiling a laser ablation of corneal tissue according to claim 16, further comprising:

means for splitting said ablating laser beam to provide a first split beam adapted to ablate said collagen material and a second split beam adapted to ablate said corneal tissue;

wherein said collagen material and said corneal tissue are substantially simultaneously ablated.

23. The apparatus for profiling a laser ablation of corneal tissue according to claim 22, wherein:

said collagen material is a cross-linked collagen material.

24. The apparatus for profiling a laser ablation of corneal tissue according to claim 16, further comprising:

a printer to print a representation of said measured actual ablation profile achieved in said collagen material.

* * * * *